(12) United States Patent
Aghaei Amirkhizi et al.

(10) Patent No.: US 10,265,426 B2
(45) Date of Patent: Apr. 23, 2019

(54) SCANDIUM NANO-RADIOPHARMACEUTICAL

(71) Applicants: Navideh Aghaei Amirkhizi, Tehran (IR); Leila Moghaddam-Banaem, Tehran (IR); Mitra Athari Allaf, Tehran (IR); Sodeh Sajadi, Tehran (IR); Fariba Johari Daha, Tehran (IR)

(72) Inventors: Navideh Aghaei Amirkhizi, Tehran (IR); Leila Moghaddam-Banaem, Tehran (IR); Mitra Athari Allaf, Tehran (IR); Sodeh Sajadi, Tehran (IR); Fariba Johari Daha, Tehran (IR)

( * ) Notice: Subject to any disclaimer, the term of this patent is extended or adjusted under 35 U.S.C. 154(b) by 0 days.

(21) Appl. No.: 15/796,775

(22) Filed: Oct. 28, 2017

(65) Prior Publication Data

US 2018/0055955 A1 Mar. 1, 2018

Related U.S. Application Data

(60) Provisional application No. 62/435,884, filed on Dec. 19, 2016.

(51) Int. Cl.

| | |
|---|---|
| *A61K 9/00* | (2006.01) |
| *A61K 51/12* | (2006.01) |
| *A61K 51/06* | (2006.01) |
| *G21G 1/06* | (2006.01) |
| *A61P 35/00* | (2006.01) |
| *G21G 1/00* | (2006.01) |

(52) U.S. Cl.
CPC .......... *A61K 51/1251* (2013.01); *A61K 51/06* (2013.01); *A61K 51/065* (2013.01); *A61P 35/00* (2018.01); *G21G 1/06* (2013.01); *G21G 1/001* (2013.01); *G21Y 2002/104* (2013.01)

(58) Field of Classification Search
CPC .................................................. A61K 51/1251
See application file for complete search history.

(56) References Cited

U.S. PATENT DOCUMENTS

| 5,338,532 A | * | 8/1994 | Tomalia ................ A01N 25/10 |
| | | | 424/1.49 |
| 6,224,536 B1 | | 5/2001 | Pike |
| 2013/0336888 A1 | | 12/2013 | Babich et al. |

OTHER PUBLICATIONS

Cutler, Radiometals for Combined Imaging and Therapy, Chemical Reviews, 2013, 113, 858-883.*
Ting, G., C.-H. Chang, and H.-E. Wang, Cancer nanotargeted radiopharmaceuticals for tumor imaging and therapy. Anticancer Research, 2009. vol. 29(issue 10): pp. 4107-4118.

(Continued)

*Primary Examiner* — Paul W Dickinson
(74) *Attorney, Agent, or Firm* — Bajwa IP Law Firm; Haris Zaheer Bajwa

(57) ABSTRACT

Disclosed herein is a method for preparing a scandium nano-radiopharmaceutical. The method comprises forming a plurality of scandium-encapsulated dendrimers by encapsulating scandium in polyamidoamine (PAMAM) dendrimers with amine surface groups, and forming a scandium nano-radiopharmaceutical by irradiating the plurality of scandium-encapsulated dendrimers by bombarding neutrons toward the scandium-encapsulated dendrimers.

11 Claims, 18 Drawing Sheets

(56) References Cited

OTHER PUBLICATIONS

Zhao, L., et al., Chlorotoxin-Conjugated Multifunctional Dendrimers Labeled with Radionuclide 131I for Single Photon Emission Computed Tomography Imaging and Radiotherapy of Gliomas. ACS Applied Materials and Interfaces, 2015. vol. 7(issue 35): pp. 19798-19808.

Ritawidya, R., et al., Synthesis and characterization of poly (amidoamine) dendrimers encapsulated 198 Au nanoparticles. Atom Indonesia, 2013. vol. 38(issue 3): pp. 118-126.

Huclier-Markai, S., et al., Chemical and biological evaluation of scandium (III)-polyaminopolycarboxylate complexes as potential PET agents and radiopharmaceuticals. Radiochimica Acta International journal for chemical aspects of nuclear science and technology, 2011. vol. 99(issue 10): pp. 653-662.

Reetz, M.T. and D. Giebel, Cross-Linked Scandium-Containing Dendrimers: A New Class of Heterogeneous Catalysts. Angewandte Chemie International Edition, 2000. vol. 39(issue 14): pp. 2498-2501.

\* cited by examiner

SCANDIUM NANO-RADIOPHARMACEUTICAL

CROSS-REFERENCE TO RELATED APPLICATION

This application claims the benefit of priority from U.S. Provisional Patent Application Ser. No. 62/435,884, filed on Dec. 19, 2016, and entitled "SCANDIUM NANO RADIO PHARMACEUTICAL FOR SOLID TUMOR TREATMENT," which is incorporated herein by reference in its entirety.

SPONSORSHIP STATEMENT

This application has been sponsored by Iran Patent Center, which does not have any rights in this application.

TECHNICAL FIELD

The present disclosure generally relates to radiopharmaceuticals, and more particularly to scandium nano-radiopharmaceuticals. Furthermore, the present disclosure relates to a method for preparing scandium nano-radiopharmaceutical.

BACKGROUND

Radiopharmaceuticals are radioactive compounds which may be utilized for diagnosis and therapeutic purposes by administering them to a patient and then monitoring via specific imaging devices. Radiopharmaceuticals which emit radiation with short path length, for example beta radiation, are used for therapy due to their characteristic of being able to lose all their energy over a very short distance; therefore, they can cause destruction of tumor cells without harming adjacent normal cells. Therapeutic radiopharmaceuticals have higher energy and stay longer in the body than other radiopharmaceuticals for increasing treatment efficiency.

Several platforms have been developed for delivery of beta radiation by encapsulating radiopharmaceuticals in different nanocarriers, for example, dendrimers to form nano-radiopharmaceuticals. Dendrimers are distinct nanostructures with different surface groups which can be used for engineering interactions between the radiopharmaceuticals and the dendrimers. Dendrimers are appropriate candidates for encapsulating metal particles, for example radioisotopes because they are structurally and chemically well-defined templates and robust stabilizers.

However, high cost of preparation, low stability, low purity, and high side effects are some of the biggest challenges in preparing nano-radiopharmaceuticals; therefore, there is a need in the art for a simple and efficient method for preparing nano-radiopharmaceuticals with high purity and high stability. Furthermore, there is a need in the art to prepare radiopharmaceuticals with minimum leakage to other organs and side effects.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes a method for preparing scandium nano-radiopharmaceuticals. The method may include forming a plurality of scandium-encapsulated dendrimers by encapsulating scandium in polyamidoamine (PAMAM) dendrimers, and forming the scandium nano-radiopharmaceuticals by bombarding neutrons toward the plurality of scandium-encapsulated dendrimers.

The above general aspect may include one or more of the following features. In one exemplary embodiment, the PAMAM dendrimers may include PAMAM dendrimers with amine surface groups. In an exemplary embodiment, bombarding neutrons toward the plurality of scandium-encapsulated dendrimers may include bombarding neutrons toward the scandium-encapsulated dendrimers with a neutron flux between about $3 \times 10^{11}$ and about $5 \times 10^{11}$ n·cm$^{-2}$ s$^{-1}$ (neutrons per cm$^2$ per second) for a period of time less than about 3 hours.

According to some implementations, forming a plurality of scandium-encapsulated dendrimers may include forming a Sc$^{3+}$-PAMAM solution by mixing a Sc(NO$_3$)$_3$ solution with a PAMAM solution, and forming a solution of the plurality of scandium-encapsulated dendrimers by reducing the Sc$^{3+}$-PAMAM solution. In an exemplary embodiment, forming a plurality of scandium-encapsulated dendrimers may further include drying the solution of the plurality of scandium-encapsulated dendrimers to form the plurality of scandium-encapsulated dendrimers.

According to some implementations, the Sc(NO$_3$)$_3$ solution may include Sc(NO$_3$)$_3$ with a concentration of about 20 mM. The PAMAM solution may include PAMAM dendrimers with a concentration of about 0.01 mM. In some exemplary embodiments, the PAMAM solution may include PAMAM dendrimers with a generation of at least 4.

According to some implementations, the PAMAM solution may include PAMAM dendrimers with amine surface groups. The Sc$^{3+}$ may be present in the Sc$^{3+}$-PAMAM solution with an amount between about 50 and about 60 Sc$^{3+}$ ions per PAMAM dendrimer. According to some implementations, the scandium nano-radiopharmaceutical may include one of scandium-47 ($^{47}$Sc), or scandium-46 ($^{46}$Sc), or combinations thereof.

According to some implementations, forming a solution of the plurality of scandium-encapsulated dendrimers by reducing the Sc$^{3+}$-PAMAM solution may include adjusting pH of the Sc$^{3+}$-PAMAM solution to a pH between about 6 and about 8, forming a solution of the plurality of scandium-encapsulated dendrimer by adding a reducing agent to the Sc$^{3+}$-PAMAM solution, and adjusting pH of the solution of the plurality of scandium-encapsulated dendrimer to a pH between about 2 and about 4.

In another general aspect, the present disclosure describes a scandium nano-radiopharmaceutical for treating solid tumors. The scandium nano-radiopharmaceutical may include scandium (Sc) particles which may be encapsulated within polyamidoamine (PAMAM) dendrimers. The Sc particles may be present in the scandium nano-radiopharmaceutical with an amount of between 50 Sc particles per PAMAM dendrimer and 60 Sc particles per PAMAM dendrimer.

The above general aspect may include one or more of the following features. In one exemplary embodiment, the Sc particles may include radioactive Sc particles. The PAMAM solution may include PAMAM dendrimers with a generation of at least 4. The PAMAM solution may include PAMAM dendrimers with amine surface groups. The scandium nano-radiopharmaceutical may include one of scandium-47 ($^{47}$Sc) particles, scandium-46 ($^{46}$Sc) particles, or combinations thereof.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples to provide a thorough understanding of the relevant teachings related to the exemplary embodiments. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be plain to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Disclosed herein is a scandium nano-radiopharmaceutical and the preparation method thereof. Scandium may be utilized for conjugating to a dendrimer as a nanocarriers to form scandium nano-radiopharmaceutical. The scandium nano-radiopharmaceutical may include scandium particles which may be encapsulated within polyamidoamine (PAMAM) dendrimers. The scandium nano-radiopharmaceutical with encapsulated scandium particles may be used for treating solid tumors, such as breast tumors and prostate tumors, through emitting beta radiation towards tumor cells, and then destroying the tumor cells.

Figure 1A:
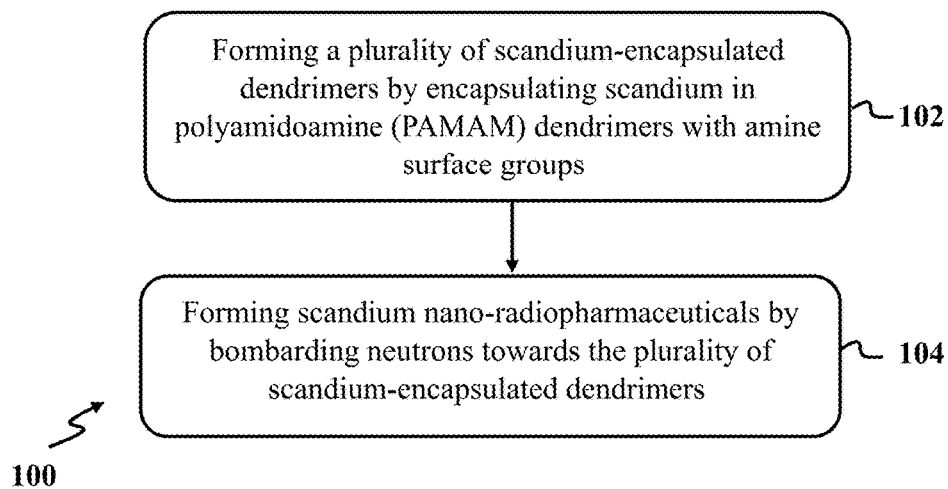
FIG. 1A illustrates a method for preparing scandium nano-radiopharmaceuticals, consistent with one or more exemplary embodiments of the present disclosure.

FIG. 1A shows method 100 for preparing scandium nano-radiopharmaceuticals, consistent with an exemplary embodiment of the present disclosure. Method 100 may include forming a plurality of scandium-encapsulated dendrimers by encapsulating scandium within polyamidoamine (PAMAM) dendrimers with amine surface groups (step 102), and forming a scandium nano-radiopharmaceutical by bombarding neutrons toward the plurality of scandium-encapsulated dendrimers (step 104).

Figure 1B:
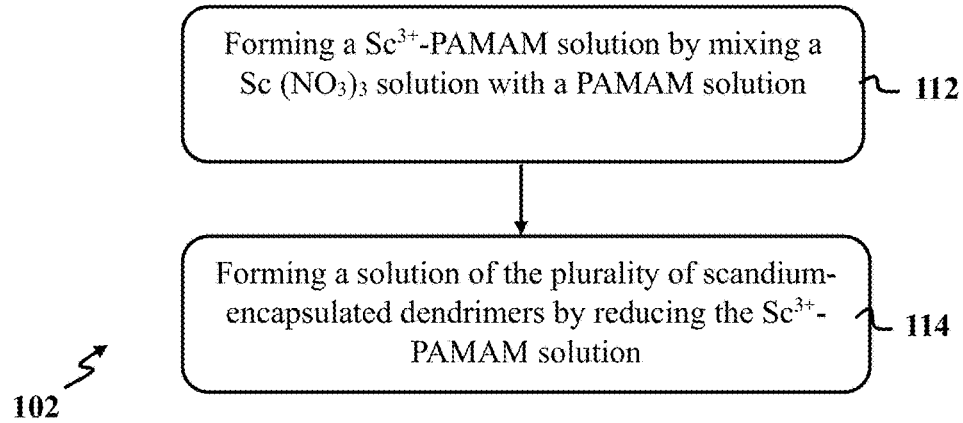
FIG. 1B illustrates a method for forming a plurality of scandium-encapsulated dendrimers by encapsulating scandium in polyamidoamine (PAMAM) dendrimers, consistent with one or more exemplary embodiments of the present disclosure.

Step 102 may include forming a plurality of scandium-encapsulated dendrimers by encapsulating scandium within polyamidoamine (PAMAM) dendrimers with amine surface groups. FIG. 1B shows an exemplary implementation of step 102 for forming a plurality of scandium-encapsulated dendrimers by encapsulating scandium in polyamidoamine (PAMAM) dendrimers, consistent with an exemplary embodiment of the present disclosure. Forming the plurality of scandium-encapsulated dendrimers may include forming a $Sc^{3+}$-PAMAM solution by mixing a $Sc(NO_3)_3$ solution with a PAMAM solution (step 112), and forming a solution of the plurality of scandium-encapsulated dendrimers by reducing the $Sc^{3+}$-PAMAM solution (step 114).

Figure 2A:
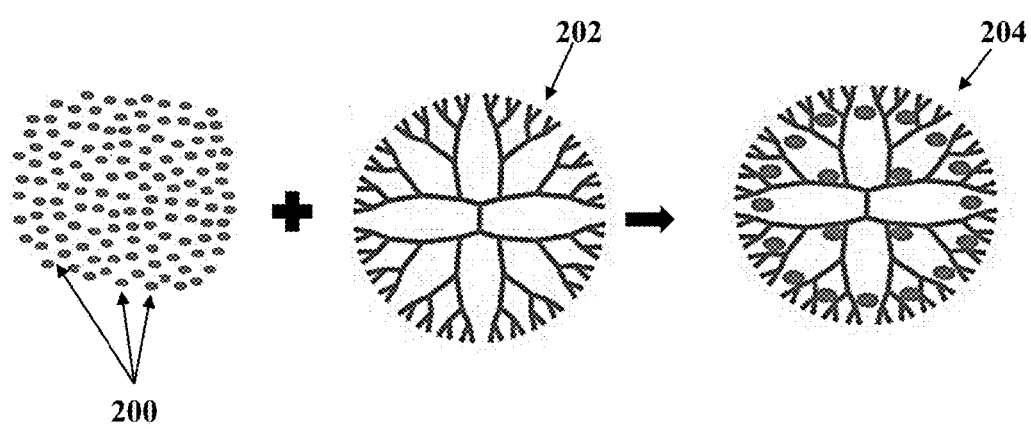
FIG. 2A illustrates a schematic of forming a $Sc^{3+}$-PAMAM solution through mixing a $Sc(NO_3)_3$ solution with a PAMAM solution, consistent with one or more exemplary embodiments of the present disclosure.

FIG. 2A shows a schematic an exemplary implementation of step 112 of forming a $Sc^{3+}$-PAMAM solution by mixing a $Sc(NO_3)_3$ solution with a PAMAM solution. Step 112 may include forming a $Sc^{3+}$-PAMAM solution including $Sc^{3+}$-PAMAM dendrimers 204 through mixing a $Sc(NO_3)_3$ solution including scandium ions ($Sc^{3+}$) 200 with a PAMAM solution including PAMAM dendrimers 202.

In step 112, mixing the $Sc(NO_3)_3$ solution with the PAMAM solution may include stirring the $Sc(NO_3)_3$ solution including scandium ions ($Sc^{3+}$) 200 and the PAMAM solution including PAMAM dendrimers 202. In an exemplary embodiment, mixing the $Sc(NO_3)_3$ solution including scandium ions ($Sc^{3+}$) 200 with the PAMAM solution may be done using a magnet stirrer for a period of time between about 15 minutes and about 25 minutes under nitrogen atmosphere.

In an exemplary implementation, the $Sc(NO_3)_3$ solution may include $Sc(NO_3)_3$ with a concentration of about 20 mM. The PAMAM solution may include PAMAM dendrimers with a concentration of about 0.01 mM. Moreover, the PAMAM solution may include PAMAM dendrimers 202 with a generation of at least 4 and the PAMAM dendrimers 202 may include amine surface groups. In an exemplary implementation, the $Sc^{3+}$ ions 200 may be present in the $Sc^{3+}$-PAMAM solution with an amount of between about 50 $Sc^{3+}$ ions per PAMAM dendrimer and about 60 $Sc^{3+}$ ions per PAMAM dendrimer.

Figure 1C:
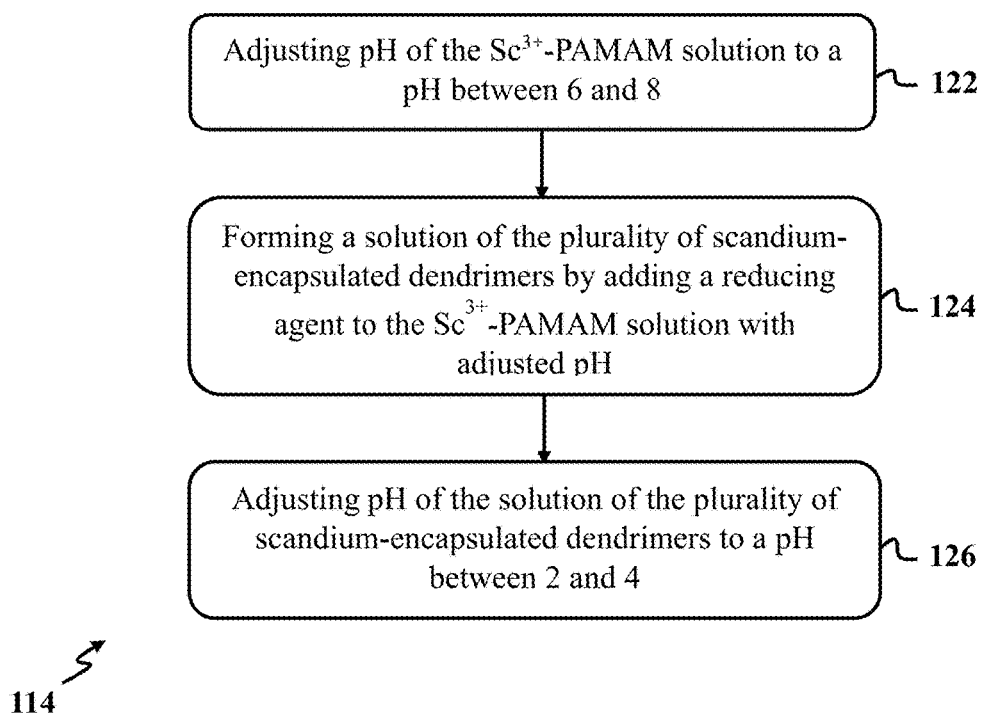
FIG. 1C illustrates a method for forming the solution of the plurality of scandium-encapsulated dendrimers through reducing the $Sc^{3+}$-PAMAM solution, consistent with one or more exemplary embodiments of the present disclosure.
Figure 2B:
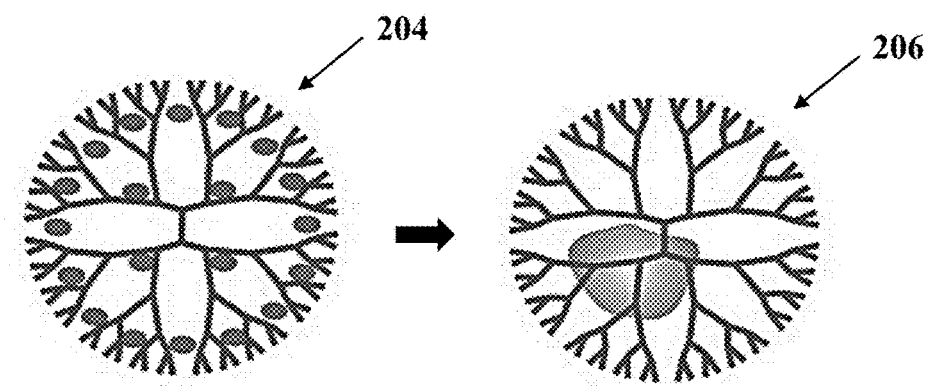
FIG. 2B illustrates a schematic of forming a solution of the plurality of scandium-encapsulated dendrimers through reducing the $Sc^{3+}$-PAMAM solution, consistent with one or more exemplary embodiments of the present disclosure.

Step 114 may include forming a solution of the plurality of scandium-encapsulated dendrimers through reducing the $Sc^{3+}$-PAMAM solution including $Sc^{3+}$-PAMAM dendrimers. FIGS. 1C and 2B in combination illustrate exemplary aspects of step 114. FIG. 2B shows a schematic an exemplary implementation of step 114 of forming a solution of the plurality of scandium-encapsulated dendrimers through reducing the $Sc^{3+}$-PAMAM solution.

FIG. 1C shows an exemplary process of step 114 for forming the solution of the plurality of scandium-encapsulated dendrimers 206 through reducing the $Sc^{3+}$-PAMAM solution including $Sc^{3+}$-PAMAM dendrimers 204, consistent with an exemplary embodiment of the present disclosure. Referring to FIG. 1C, forming the solution of the plurality of scandium-encapsulated dendrimers may include adjusting pH of the $Sc^{3+}$-PAMAM solution to a pH between about 6 and about 8 (step 122), forming a solution of the plurality of scandium-encapsulated dendrimers by adding a reducing agent to the $Sc^{3+}$-PAMAM solution with adjusted pH (step 124), and adjusting pH of the solution of the plurality of scandium-encapsulated dendrimer to a pH between about 2 and about 4 (step 126).

Step 122 may include adjusting pH of the $Sc^{3+}$-PAMAM solution including $Sc^{3+}$-PAMAM dendrimers 204 to a pH between about 6 and about 8. In this step, pH of the $Sc^{3+}$-PAMAM solution including $Sc^{3+}$-PAMAM dendrimers 204 may be adjusted to a pH between 6 and 8 by addition of a base compound to the $Sc^{3+}$-PAMAM solution, for example, NaOH.

Step 124 may include forming a solution of the plurality of scandium-encapsulated dendrimers 206 by adding a reducing agent to the $Sc^{3+}$-PAMAM solution including $Sc^{3+}$-PAMAM dendrimers 204 with an adjusted pH.

In step 124, a solution of the plurality of scandium-encapsulated dendrimers 206 may be formed by adding a reducing agent, for example, $NaBH_4$, to the $Sc^{3+}$-PAMAM solution. The reducing agent may be used to reduce the $Sc^{3+}$ ions in the $Sc^{3+}$-PAMAM solution to zero-valent Sc particles which may be encapsulated within the PAMAM dendrimers.

Step 126 may include adjusting pH of the solution of the plurality of scandium-encapsulated dendrimer 206 to a pH between about 2 and about 4. In this step, extra amount of the reducing agent may be decomposed through adjusting pH of the solution of the plurality of scandium-encapsulated dendrimer 206 to a pH between about 2 and about 4.

In an exemplary embodiment, adjusting pH of the solution of the plurality of scandium-encapsulated dendrimer 206 may be done by adding an acid compound, for example, $HClO_4$ to the solution of the plurality of scandium-encapsulated dendrimer 206. After adjusting pH of the solution of the plurality of scandium-encapsulated dendrimer, in order to complete encapsulation of scandium in PAMAM dendrimers, the reduced $Sc^{3+}$-PAMAM solution may be stirred under the nitrogen atmosphere using a magnet stirrer for at least about 2 hours.

In an exemplary embodiment, forming the plurality of scandium-encapsulated dendrimers may include drying the solution of the plurality of scandium-encapsulated dendrimers to form the plurality of scandium-encapsulated dendrimers. The solution of the plurality of scandium-encapsulated dendrimers may be dried using an oven for a period of time about 24 hours.

Referring back to FIG. 1A, step 104 may include forming a scandium nano-radiopharmaceutical by bombarding neutrons toward the plurality of scandium-encapsulated dendrimers. Bombarding neutrons toward the plurality of scandium-encapsulated dendrimers may include bombarding neutrons toward the scandium-encapsulated dendrimers over a time period of less than 3 hours.

In an exemplary embodiment, bombarding neutrons toward the scandium-encapsulated dendrimers may include bombarding neutrons toward the scandium-encapsulated dendrimers with a neutron flux between about $3\times10^{11}$ and about $5\times10^{11}$ $n\cdot cm^{-2}$ $s^{-1}$ (neutrons per cm2 per second).

In step 104, due to bombarding neutrons toward the plurality of scandium-encapsulated dendrimers, scandium particles may be activated and converted to one of scandium-47 ($^{47}Sc$) radioactive isotope, scandium-46 ($^{46}Sc$) radioactive isotopes or combinations thereof. Moreover, placing the scandium-encapsulated dendrimers in the heart of the reactor may cause the scandium-encapsulated dendrimers to be burnt; therefore, they may be placed in a position away from heart of the reactor, where the intensity of the radiation may be lower than the heart of the reactor, for example at a pile position.

In some exemplary implementations, after preparing the scandium nano-radiopharmaceuticals, the scandium nano-radiopharmaceuticals may be used for treating solid tumors through administering a solution of the scandium nano-radiopharmaceutical to solid tumor cells. Administering the scandium nano-radiopharmaceuticals to solid tumor cells may include injecting the nano-radiopharmaceutical to a solid tumor site, emitting beta radiation from the nano-radiopharmaceutical toward the solid tumor cells, and, therefore, killing tumor cells responsive to the emitted beta radiation through absorbing the beta radiation by the tumor cells.

In an exemplary embodiment, injecting the scandium nano-radiopharmaceutical to a solid tumor site may include direct injection of the scandium nano-radiopharmaceutical to the solid tumor site. Presence of the PAMAM dendrimers may enhance adhesion of the scandium nano-radiopharmaceuticals to the solid tumor site; therefore, it may prevent the leakage of the scandium nano-radiopharmaceuticals to other parts of body and their side effects.

In some exemplary implementations, after injecting the scandium nano-radiopharmaceuticals to the solid tumor site, the scandium nano-radiopharmaceuticals may emit beta radiation with short path length toward the solid tumor cells. For example, energy of the beta radiation of scandium-46 ($^{46}$Sc) in scandium nano-radiopharmaceutical may be about 357 keV with 100% abundance. As a result, the tumor cells may absorb the energy of the beta radiation and they may be killed responsive to the absorbing high energy of beta radiation.

EXAMPLES

Example 1: Preparing a Scandium Nano-Radiopharmaceutical

In this example, a scandium nano-radiopharmaceutical was prepared as follows. At first, a plurality of scandium-encapsulated dendrimers was formed by encapsulating scandium in generation 5 of polyamidoamine dendrimers with $NH_2$ surface groups (PAMAMG5-$NH_2$ dendrimer).

In order to form a plurality of scandium-encapsulated dendrimers, scandium ions ($Sc^{3+}$) were encapsulated within polyamidoamine (PAMAM) dendrimers with amine surface groups. At first, $Sc^{3+}$-PAMAM solution with a concentration of about 0.01 mM was prepared through mixing a $Sc(NO_3)_3$ solution with a PAMAM solution.

The $Sc(NO_3)_3$ solution was prepared through dissolving a plurality of $Sc_2O_3$ in a 1M $HNO_3$ solution to form the $Sc(NO_3)_3$ solution with a concentration of about 20 mM. The PAMAM solution contained PAMAMG5-$NH_2$ dendrimers which were dissolved in methanol 5% (volume/volume). The PAMAM solution had a concentration of about 0.05 mM.

Mixing the $Sc(NO_3)_3$ solution with the PAMAM solution was done though stirring using a magnet stirrer for about 20 minutes under nitrogen atmosphere. After mixing the $Sc(NO_3)_3$ solution with the PAMAM solution, the $Sc^{3+}$ ions were present in the $Sc^{3+}$-PAMAM solution with an amount of about 55 $Sc^{3+}$ ions per PAMAM dendrimer.

Then, a solution of the plurality of scandium-encapsulated dendrimers was formed through reducing the $Sc^{3+}$-PAMAM solution. In the reducing step, a reducing agent was used to reduce the $Sc^{3+}$ ions in the $Sc^{3+}$-PAMAM solution to zero-valent Sc particles which were encapsulated within the PAMAM dendrimers.

In order to reduce the $Sc^{3+}$-PAMAM solution, at first pH of the $Sc^{3+}$-PAMAM solution was adjusted to a pH of about 7.5 using a NaOH solution with a concentration of 2 M. Then, a solution of the plurality of scandium-encapsulated dendrimers was formed through adding $NaBH_4$ with a molar ratio of about 3:1 ($NaBH_4$:$Sc^{3+}$ particles) as a reducing agent to the $Sc^{3+}$-PAMAM solution. The reducing step of the $Sc^{3+}$-PAMAM solution was done under nitrogen atmosphere.

After that, decomposing the excess amount of $BH_4^-$ was done by adjusting pH of the solution of the plurality of scandium-encapsulated dendrimer to a pH about 3 using $HClO_4$ with a concentration of about 70.0% (volume/volume). Then, in order to complete encapsulation of scandium in PAMAM dendrimers, the reduced $Sc^{3+}$-PAMAM solution was stirred under the nitrogen atmosphere using a magnet stirrer for about 2 hours.

Finally, scandium nano-radiopharmaceuticals were formed by irradiating the plurality of scandium-encapsulated dendrimers. The plurality of scandium-encapsulated dendrimers was flame sealed into a quartz ampoule, and then sealed in a cold-welding aluminium can. Irradiating the plurality of scandium-encapsulated dendrimers was done by bombarding neutrons toward the quartz ampule containing scandium-encapsulated dendrimers for about 2 hours in Tehran Research Reactor (TRR) by a neutron flux of about $3\times10^{11}$ n·cm$^{-2}$ s$^{-1}$ (neutrons per cm2 per second).

Placing the quartz ampule containing scandium-encapsulated dendrimers in the heart of the reactor causes the scandium-encapsulated dendrimers to be burnt; therefore, the quartz ampule containing scandium-encapsulated dendrimers was placed in a pile position of the reactor away from heart of the reactor. Due to irradiating the plurality of scandium-encapsulated dendrimers, scandium particles were activated and converted to radioactive scandium-46 ($^{46}$Sc) particles.

After irradiating the plurality of scandium-encapsulated dendrimers, the quartz ampule containing the scandium nano-radiopharmaceuticals was cooled for at least 6 hours under nitrogen atmosphere to reduce short-lived activity of some impurities, such as sodium from the reducing agent $NaBH_4$, in the aluminium can. The half-life of sodium (Na) is short and about 15 hours; therefore, this sodium impurity was decayed after 24 hours, and the scandium nano-radiopharmaceuticals with high purity were obtained.

Example 2: Characterization of the Scandium Nano-Radiopharmaceutical

In this example, the scandium nano-radiopharmaceuticals and the scandium-encapsulated dendrimers were characterized through different techniques, such as a scanning electron microscopy (SEM), a high resolution transmission electron microscopy (HRTEM), and a dynamic light scattering (DLS). Moreover, purity of the scandium nano-radiopharmaceuticals was tested by quality control tests such as an instant thin layer chromatography (ITLC), and a high-pressure liquid chromatography (HPLC).

Figure 3A:
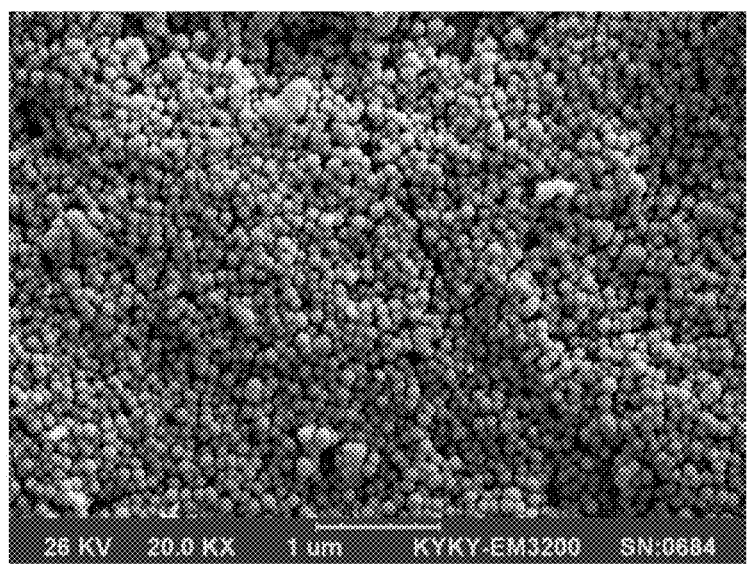
FIG. 3A illustrates a scanning electron microscopy (SEM) image of scandium-encapsulated dendrimers, consistent with one or more exemplary embodiments of the present disclosure.

FIG. 3A illustrates a scanning electron microscopy (SEM) image of scandium-encapsulated dendrimers, consistent with an exemplary embodiment of the present disclosure. The SEM image was taken with a digital scanning electron microscope with a resolution of about 6.00 nm. Referring to FIG. 3A, the scandium-encapsulated dendrimers are homogenous spherical particles with a diameter between about 3 nm and about 5 nm. In these scandium-encapsulated dendrimers, the scandium particles are encapsulated within PAMAM dendrimers with a generation of 5.

Figure 3B:
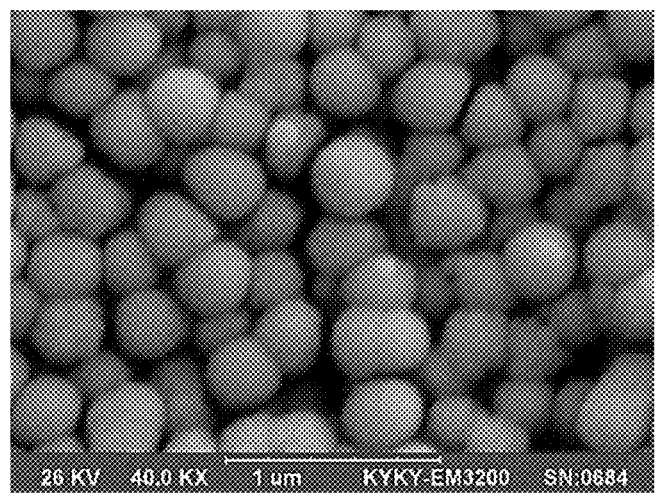
FIG. 3B illustrates a scanning electron microscopy (SEM) image of scandium nano-radiopharmaceuticals, consistent with one or more exemplary embodiments of the present disclosure.

FIG. 3B illustrates a scanning electron microscopy (SEM) image of scandium nano-radiopharmaceuticals, consistent with an exemplary embodiment of the present disclosure. Referring to FIG. 3B, the scandium nano-radiopharmaceuticals have a larger particle size than scandium-encapsulated dendrimers of FIG. 3A. The larger particle size of the scandium nano-radiopharmaceuticals may be a result of irradiating scandium-encapsulated dendrimers to form scandium nano-radiopharmaceuticals.

Figure 4A:
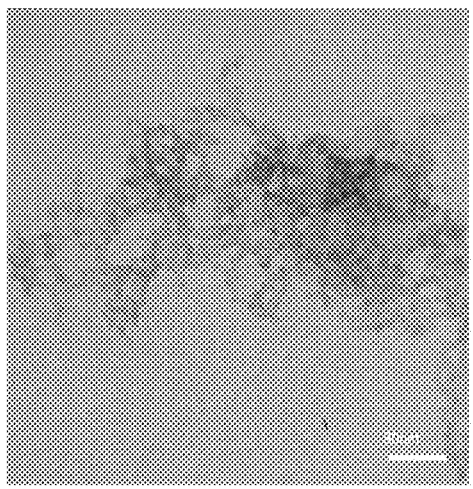
FIG. 4A illustrates a high-resolution transmission electron microscopy (HRTEM) image of scandium-encapsulated dendrimers, consistent with one or more exemplary embodiments of the present disclosure.
Figure 4B:
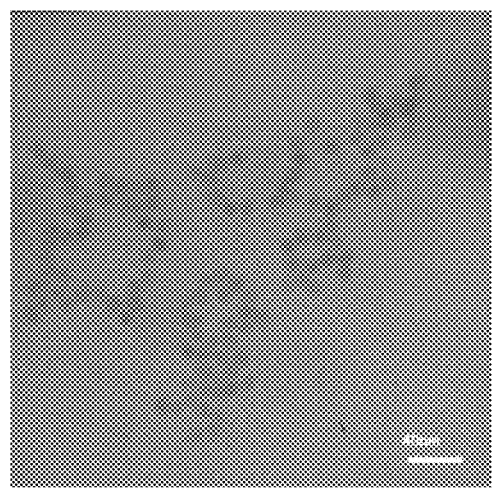
FIG. 4B illustrates a magnified high-resolution transmission electron microscopy (HRTEM) image of scandium-encapsulated dendrimers, consistent with one or more exemplary embodiments of the present disclosure.

FIG. 4A illustrates a high-resolution transmission electron microscopy (HRTEM) image of scandium-encapsulated dendrimers with a resolution of about 5 nm in a scale of 80 nm, consistent with an exemplary embodiment of the present disclosure. FIG. 4B illustrates a high-resolution transmission electron microscopy (HRTEM) image of scandium-encapsulated dendrimers with a resolution of about 5 nm in a scale of 40 nm, consistent with an exemplary embodiment of the present disclosure.

HRTEM images were obtained with a transmission electron microscope which has a point-to-point resolution of about 0.23 nm. Referring to FIGS. 4A and 4B, the HRTEM images show no agglomeration in the scandium-encapsulated dendrimers. Also, HRTEM images illustrate that the scandium-encapsulated dendrimers are monodisperse spherical particles and have a particles size between about 3 nm and about 5 nm.

Figure 5:
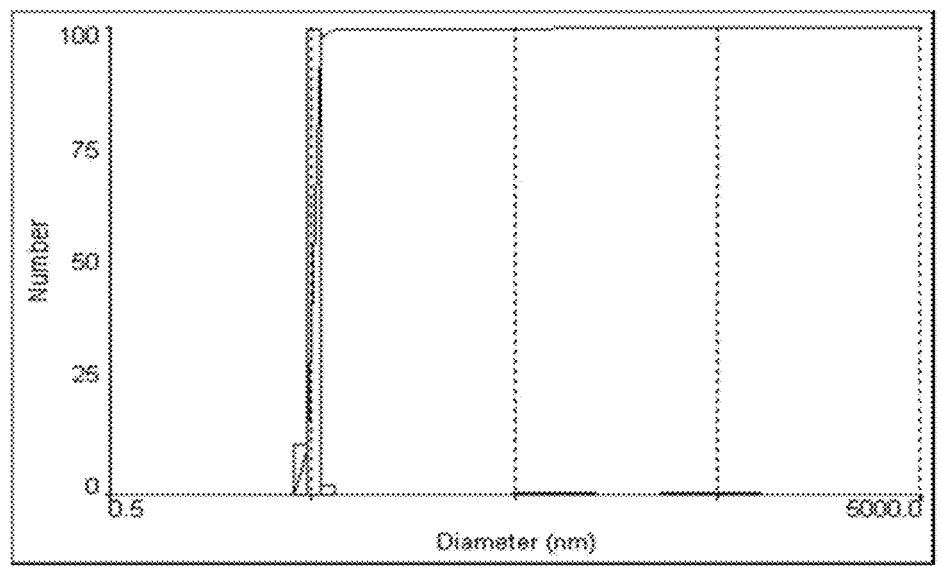
FIG. 5 illustrates a dynamic light scattering (DLS) graph of scandium-encapsulated dendrimers, consistent with one or more exemplary embodiments of the present disclosure.

FIG. 5 illustrates a dynamic light scattering (DLS) graph of scandium-encapsulated dendrimers, consistent with an exemplary embodiment of the present disclosure. Referring to FIG. 5, the scandium-encapsulated dendrimers have a uniform size distribution and they have a particle size between about 3 nm and 5 nm.

Figure 6A:
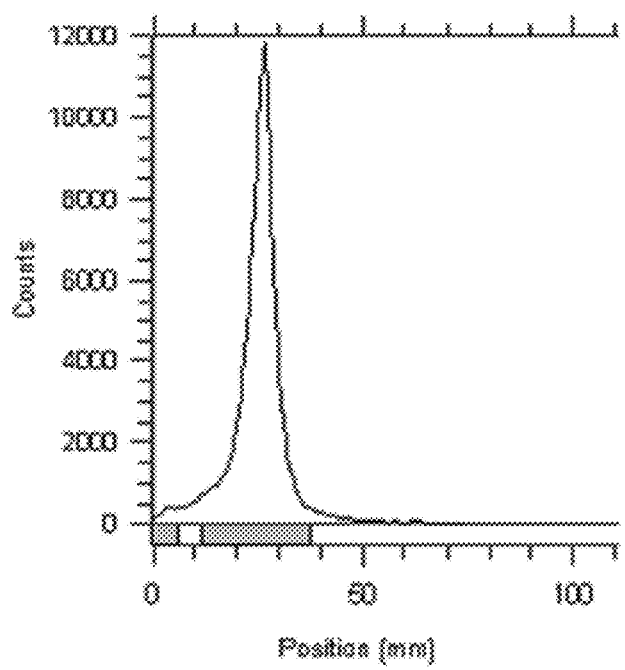
FIG. 6A illustrates an instant thin-layer chromatography (ITLC) graph of $ScCl_3$, consistent with one or more exemplary embodiments of the present disclosure.

Radiochemical purity of the scandium nano-radiopharmaceuticals was evaluated by performing an instant thin-layer chromatography (ITLC). FIG. 6A illustrates an instant thin layer chromatography (ITLC) graph of $ScCl_3$, consistent with an exemplary embodiment of the present disclosure. Referring to FIG. 6A, radiochemical purity of the scandium particles was ascertained by using ITLC.

Figure 6B:
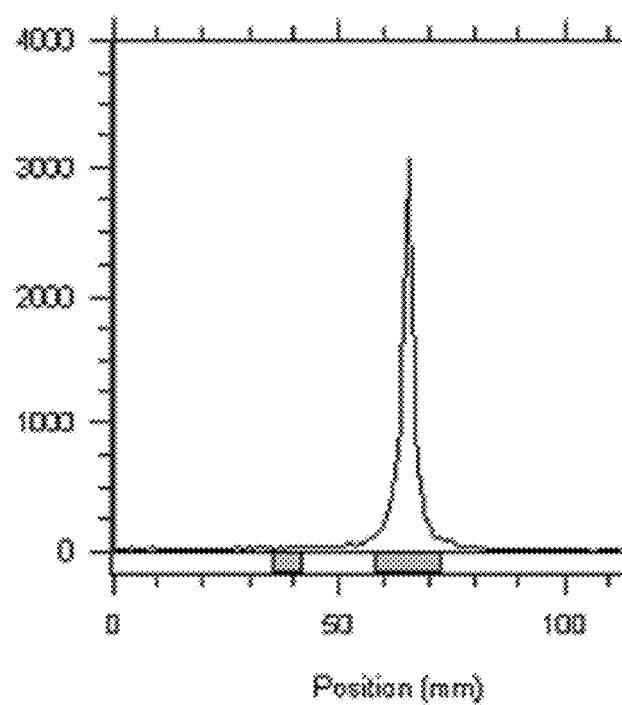
FIG. 6B illustrates an instant thin-layer chromatography (ITLC) graph of scandium-encapsulated dendrimers, consistent with one or more exemplary embodiments of the present disclosure.

FIG. 6B illustrates an instant thin layer chromatography (ITLC) graph of the scandium nano-radiopharmaceuticals, consistent with an exemplary embodiment of the present disclosure. Referring to FIG. 6B, the scandium nano-radiopharmaceuticals have a high radiochemical purity which is more than 99%.

Referring to FIGS. 6A and 6B, the ITLC graph of $ScCl_3$ has a peak at a position of about 37 mm, and the ITLC graph of the scandium nano-radiopharmaceuticals has a peak at a position of about 65 mm. Therefore, this shift toward higher positions confirms encapsulation of the scandium particles within PAMAM dendrimers.

Figure 7:
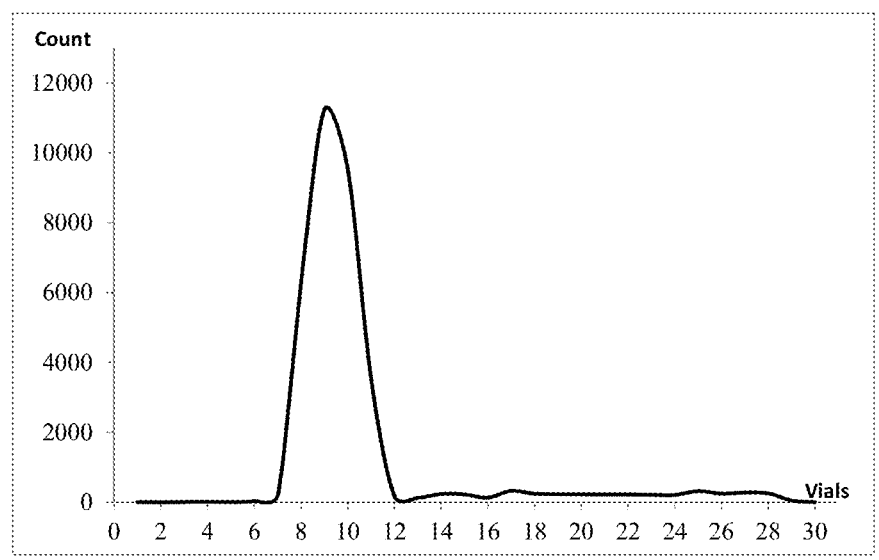
FIG. 7 illustrates a high-pressure liquid chromatography (HPLC) graph of scandium-encapsulated dendrimers, consistent with one or more exemplary embodiments of the present disclosure.

Further confirmation of the chemical purity of the scandium-encapsulated dendrimers was provided with a high-pressure liquid chromatography (HPLC). FIG. 7 illustrates a HPLC graph of the scandium-encapsulated dendrimers, consistent with an exemplary embodiment of the present disclosure. Referring to FIG. 7 the peak of the HPLC graph shows that scandium-encapsulated dendrimers have a high chemical purity which is more than 97%.

Figure 8:
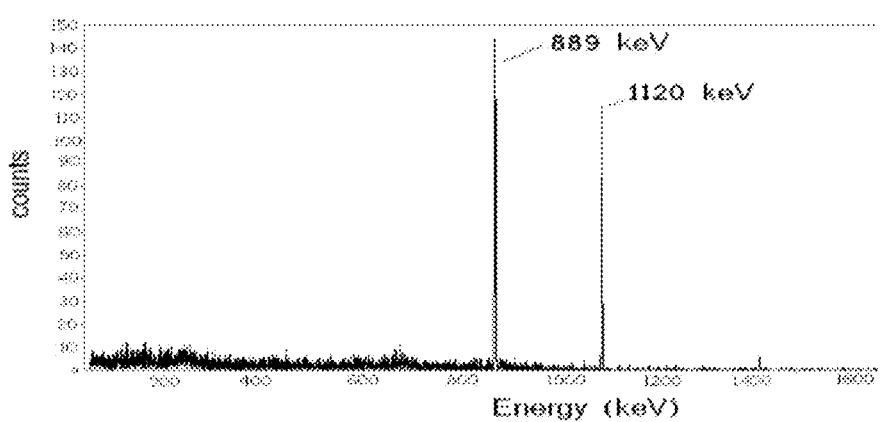
FIG. 8 illustrates a gamma spectrometry of scandium nano-radiopharmaceutical, consistent with one or more exemplary embodiments of the present disclosure.

In order to evaluate radionuclide purity of the scandium nano-radiopharmaceuticals, gamma spectroscopy was done. FIG. 8 illustrates gamma spectrometry of scandium nano-radiopharmaceutical, consistent with an exemplary embodiment of the present disclosure. Referring to FIG. 8, the gamma spectroscopy shows the exact gamma energies of the scandium nano-radiopharmaceutical which are about 889 and about 1120 keV; therefore, the scandium nano-radiopharmaceutical has a high radionuclide purity.

Example 3: In-Vivo Studies of the Scandium Nano-Radiopharmaceuticals

In this example, in-vivo studies of the scandium nano-radiopharmaceutical. The in-vivo studies were a biodistribution analysis and an evaluation of the efficiency of the scandium nano-radiopharmaceuticals in treating solid tumors. The animal experiments were performed in accordance with the Principles of Laboratory Animal Care.

These in-vivo studies were done on 20 female BALB/c mice with a body weight of about 18 grams. The mice were between 6- and 8-week-old, and they were housed in stainless steel cages in a ventilated animal room. Room temperature was maintained at about 20±2° C., and the relative humidity was about 60±10%. Moreover, 4T1 cells were purchased from Pasteur Institute of Iran.

After cell culture, the 4T1 cells were injected under a part of skin in the breast site of mice for creating solid breast tumors. These in-vivo studies were done by administering a solution of the scandium nano-radiopharmaceutical with a pH of about 7. The solution of the scandium nano-radiopharmaceutical was prepared by dissolving a plurality of the scandium nano-radiopharmaceutical in a phosphate-buffered saline (PBS) solution.

The biodistribution of the scandium nano-radiopharmaceuticals was evaluated as follows. The study was performed on 12 solid tumor-bearing mice between 7 and 10 days after injecting the 4T1 cells, when the diameter of solid tumor mass was about 1 cm. At first, 0.1 mL of scandium nano-radiopharmaceutical solution with a radioactivity of about 7.4 MBq/mL (megabecquerel per ml) was intravenously injected into the tail vein of each mouse.

Then, the animals were sacrificed under CO2 atmosphere at specified time intervals of 4, 24 and 48 hours. After that, the specific activity of different organs, such as blood, heart, lung adrenal, stomach, intestine, liver, spleen, kidney, muscle, brain, tumor, and bone was calculated as the percentage of injected dose of the scandium nano-radiopharmaceutical solution per gram of each organ (% ID/g) using a gamma counter detector.

Figure 9:
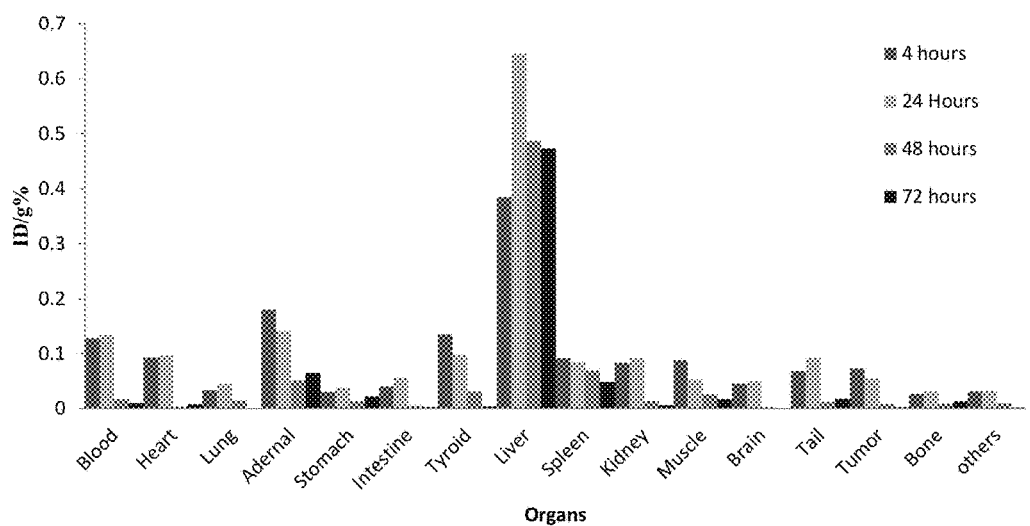
FIG. 9 illustrates biodistribution of scandium nano-radiopharmaceutical in different mice organs, consistent with one or more exemplary embodiments of the present disclosure.

FIG. 9 illustrates biodistribution of injected scandium nano-radiopharmaceutical in different mouse organs, consistent with an exemplary embodiment of the present disclosure. Referring to FIG. 9, comparison between ID/g percentages of different organs illustrates that the livers of mice have the highest accumulation of injected scandium nano-radiopharmaceutical solution per gram of liver organ (% ID/g).

In order to evaluate the efficiency of the scandium nano-radiopharmaceuticals in treating solid-tumors, 0.1 ml of scandium nano-radiopharmaceutical solution with a radioactivity of about 3.7 MBq/ml (megabecquerel per ml) was administered to the 6 tumor-bearing mice though intra-tumor injection. Moreover, two tumor-bearing mice, C1 and C2, were specified as control groups without any administrations.

Then, 2 weeks after the injection, the tumor-bearing mice were sacrificed, and the volume of solid tumor of each mouse was measured every day in two dimensions using a sliding caliper. The tumor volume was calculated with a formula of V=(ab2)/2, where "a" stands for the long axis and "b" stands for the short axis.

Figure 10:
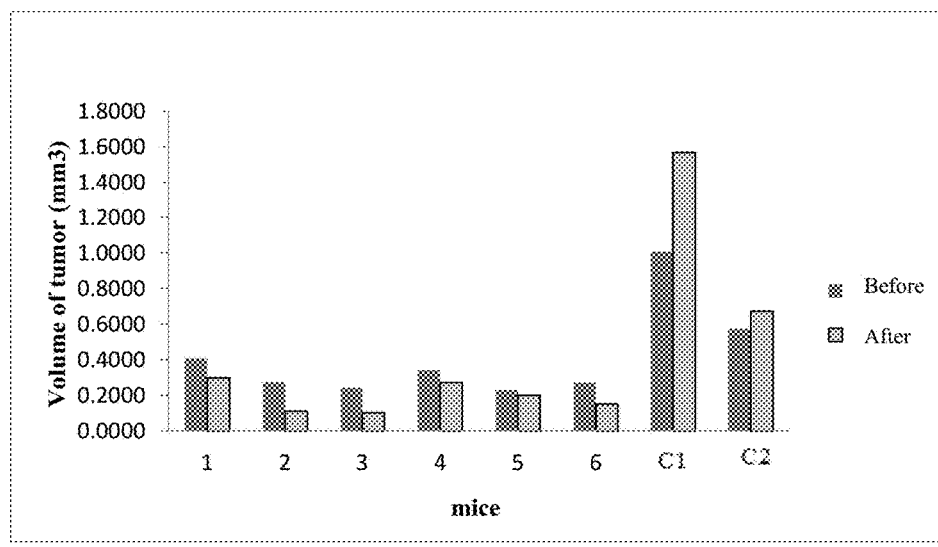
FIG. 10 illustrates volume of solid tumors before and after administration of the scandium nano-radiopharmaceutical, consistent with one or more exemplary embodiments of the present disclosure.

FIG. 10 illustrates volume of solid tumors before and after administration of the scandium nano-radiopharmaceutical, consistent with an exemplary embodiment of the present disclosure. Referring to FIG. 10, volumes of tumors in all the tumor-bearing mice with the intra-tumor injection of scandium nano-radiopharmaceutical solution are decreased after the injection. However, the volumes of tumors were increased in the two control mice of C1 and C2 without any injections. Therefore, the scandium nano-radiopharmaceutical can be considered as an effective radiopharmaceutical for treating solid tumors.

In order to further investigate the leakage of the scandium nano-radiopharmaceutical from the tumor to other organs, the tumor-bearing mice with the intra-tumor injection of scandium nano-radiopharmaceutical solution were analysed through a single-photon emission computed tomography (SPECT) two weeks after the injection.

Figure 11A:
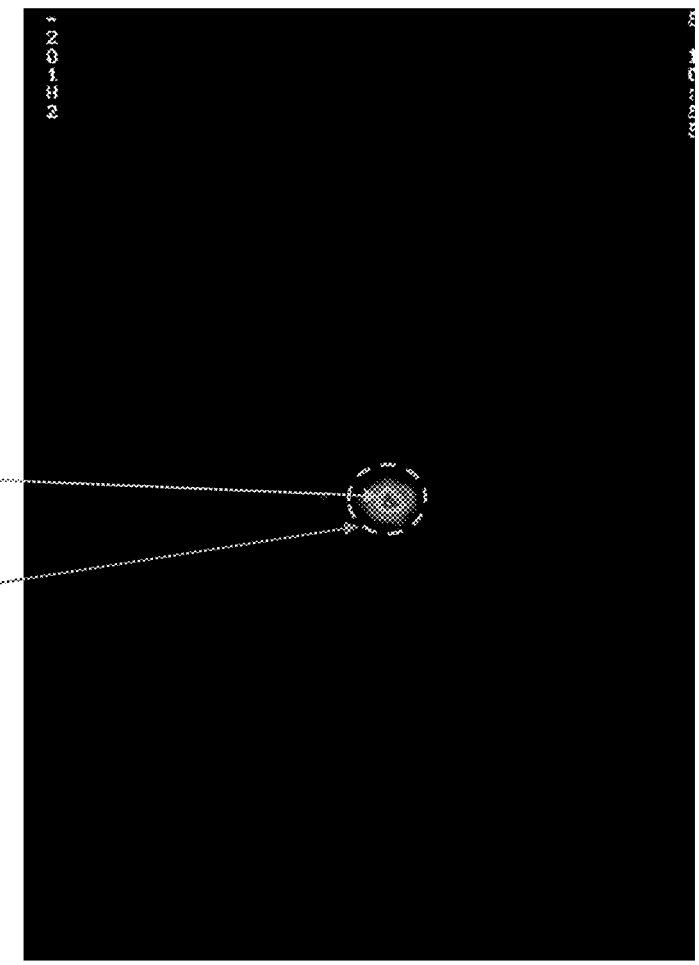
FIG. 11A illustrates a single-photon emission computed tomography (SPECT) image of an anterior view of a tumor-bearing mouse after intra-tumor injection of the scandium nano-radiopharmaceutical, consistent with one or more exemplary embodiments of the present disclosure.
Figure 11B:
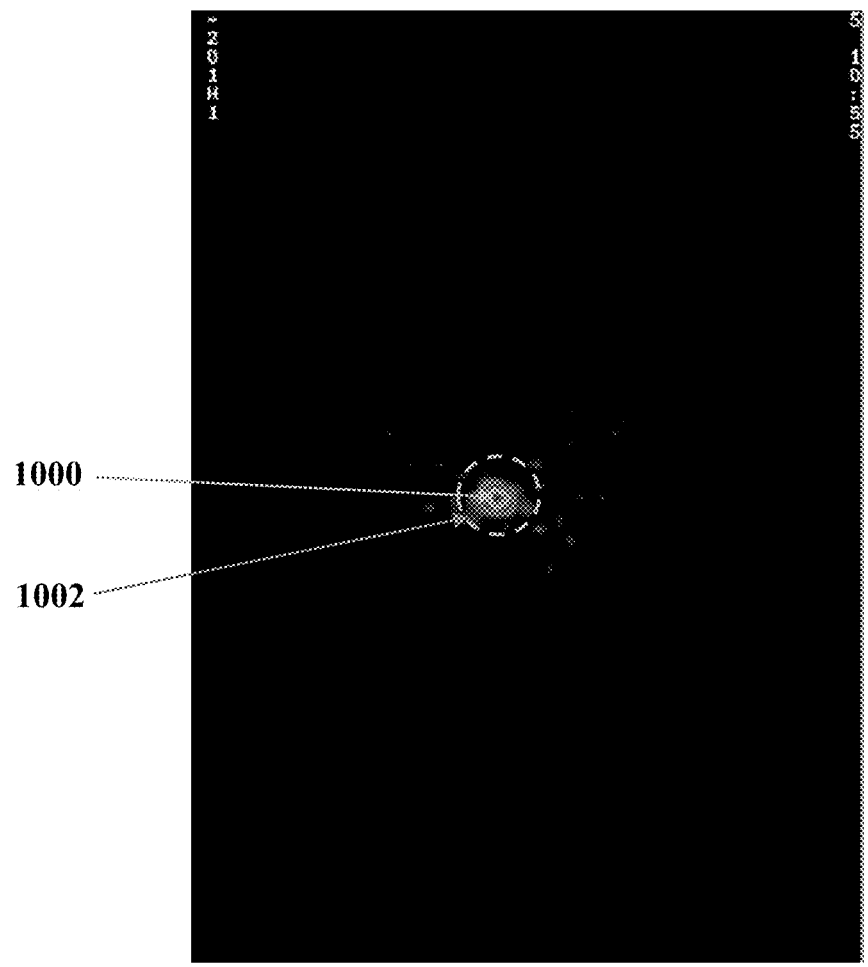
FIG. 11B illustrates a single-photon emission computed tomography (SPECT) image of a posterior view of a tumor-bearing mouse after intra-tumor injection of the scandium nano-radiopharmaceutical, with one or more exemplary embodiments of the present disclosure.

FIG. 11A illustrates a SPECT image of an anterior view of a tumor-bearing mouse after injection of the scandium nano-radiopharmaceutical 1000 to the tumor site 1002, consistent with an exemplary embodiment of the present disclosure. FIG. 11B illustrates SPECT image of a posterior view of a tumor-bearing mice after injection of the scandium nano-radiopharmaceutical 1000 to the tumor site 1002, consistent with an exemplary embodiment of the present disclosure.

Referring to FIGS. 11A and 11B, the SPECT images illustrate that the scandium nano-radiopharmaceuticals 1000 significantly stick to the tumor cells in the tumor site 1002, and they don't leak to other parts of the mouse body. Therefore, the scandium nano-radiopharmaceuticals 1000 can't reach the healthy tissues; so, they can't kill the normal cells duo to the lower level of leakage, and the scandium nano-radiopharmaceutical 1000 only can kill tumor cells in the tumor site 1002.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for preparing a scandium nano-radiopharmaceutical, comprising:
　　forming a plurality of scandium-encapsulated dendrimers by encapsulating scandium in polyamidoamine (PAMAM) dendrimers with amine surface groups, comprising:
　　　　forming a $Sc^{3+}$-PAMAM solution through mixing a $Sc(NO_3)_3$ solution with a PAMAM solution; and
　　　　forming a solution of the plurality of scandium-encapsulated dendrimers by reducing the $Sc^{3+}$-PAMAM solution; and
　　forming a scandium nano-radiopharmaceutical by bombarding neutrons towards the scandium-encapsulated dendrimers.

2. The method according to claim 1, wherein bombarding neutrons toward the scandium-encapsulated dendrimers comprises bombarding neutrons towards the scandium-encapsulated dendrimers with a neutron flux between $3 \times 10^{11}$ and $5 \times 10^{11}$ $n \cdot cm^{-2} \cdot s^{-1}$.

3. The method according to claim 2, wherein bombarding neutrons toward the scandium-encapsulated dendrimers comprises bombarding neutrons towards the scandium-encapsulated dendrimers in a time period of less than 3 hours.

4. The method according to claim 1, wherein forming the plurality of scandium-encapsulated dendrimers by encapsulating scandium in the polyamidoamine (PAMAM) dendrimers further comprises drying the solution of the plurality of scandium-encapsulated dendrimers.

5. The method according to claim 1, wherein the $Sc(NO_3)_3$ solution comprises $Sc(NO_3)_3$ with a concentration of 20 mM.

6. The method according to claim 1, wherein the PAMAM solution comprises PAMAM dendrimers with a concentration of 0.01 mM.

7. The method according to claim 1, wherein the PAMAM solution comprises PAMAM dendrimers with a generation of at least 4.

8. The method according to claim 1, wherein the PAMAM solution comprises PAMAM dendrimers with amine surface groups.

9. The method according to claim 1, wherein the $Sc^{3+}$ is present in the $Sc^{3+}$-PAMAM solution with an amount of between 50 and 60 $Sc^{3+}$ ions per PAMAM dendrimer.

10. The method according to claim 1, wherein forming the solution of the plurality of scandium-encapsulated dendrimers through reducing the $Sc^{3+}$-PAMAM solution comprises:

adjusting pH of the $Sc^{3+}$-PAMAM solution to a pH between 6 and 8;

forming a solution of the plurality of scandium-encapsulated dendrimers by adding a reducing agent to the $Sc^{3+}$-PAMAM solution with adjusted pH; and adjusting pH of the solution of the plurality of scandium-encapsulated dendrimers to a pH between 2 and 4.

11. The method according to claim 1, wherein the scandium nano-radiopharmaceutical comprises one of scandium-47 ($^{47}Sc$) and scandium-46 ($^{46}Sc$).

* * * * *